US008840562B2

(12) United States Patent
McKenna et al.

(10) Patent No.: US 8,840,562 B2
(45) Date of Patent: Sep. 23, 2014

(54) SIGNAL PROCESSING WARPING TECHNIQUE

(75) Inventors: Edward M. McKenna, Boulder, CO (US); Daniel Jon Peters, Longmont, CO (US)

(73) Assignee: Covidien LP, Mansfield, MA (US)

( * ) Notice: Subject to any disclaimer, the term of this patent is extended or adjusted under 35 U.S.C. 154(b) by 311 days.

(21) Appl. No.: 12/880,306

(22) Filed: Sep. 13, 2010

(65) Prior Publication Data

US 2011/0071378 A1 Mar. 24, 2011

Related U.S. Application Data

(60) Provisional application No. 61/245,571, filed on Sep. 24, 2009.

(51) Int. Cl.
*A61B 5/02* (2006.01)
*A61B 5/00* (2006.01)
*A61B 5/1455* (2006.01)

(52) U.S. Cl.
CPC .......... *A61B 5/14551* (2013.01); *A61B 5/6829* (2013.01); *A61B 5/726* (2013.01); *A61B 5/6838* (2013.01); *A61B 5/6816* (2013.01); *A61B 5/7264* (2013.01); *A61B 5/7207* (2013.01); *A61B 5/7203* (2013.01); *A61B 5/6826* (2013.01); *A61B 5/7221* (2013.01)
USPC .......... 600/500; 600/336; 600/364; 600/365; 600/501; 600/502; 600/503; 600/504

(58) Field of Classification Search
USPC .......... 600/364, 365, 368, 500–504, 301, 336
See application file for complete search history.

(56) References Cited

U.S. PATENT DOCUMENTS

| 4,848,901 A | 7/1989 | Hood, Jr. |
| 4,911,167 A | 3/1990 | Corenman et al. |

(Continued)

FOREIGN PATENT DOCUMENTS

| WO | WO9842249 | 10/1998 |
| WO | WO9842251 | 10/1998 |

(Continued)

OTHER PUBLICATIONS

Aoyagi, T., et al.; "Analysis of Motion Artifacts in Pulse Oximetry," *Japanese Society ME*, vol. 42, p. 20 (1993) (Article in Japanese—contains English summary of article).

(Continued)

*Primary Examiner* — Jacqueline Cheng
*Assistant Examiner* — Puya Agahi
(74) *Attorney, Agent, or Firm* — Fletcher Yoder PC

(57) ABSTRACT

Methods and systems are provided for using time-frequency warping to analyze a physiological signal. One embodiment includes applying a warping operator to the physiological signal based on the energy density of the signal. The warped physiological signal may be analyzed to determine whether non-physiological signal components are present. Further, the same warping operator may be applied to signal quality indicators, and the warped physiological signal may be analyzed based on the warped signal quality indicators. Non-physiological signal components, or types of non-physiological noise sources, may be identified based on a comparison of the physiological signal with the signal quality indicators. Non-physiological signal components may also be identified based on a neural network of known noise functions. In some embodiments, the non-physiological signal components may be removed to increase accuracy in estimating physiological parameters.

21 Claims, 3 Drawing Sheets

(56) References Cited

U.S. PATENT DOCUMENTS

| | | | |
|---|---|---|---|
| 4,934,372 | A | 6/1990 | Corenman et al. |
| 5,077,667 | A | 12/1991 | Brown et al. |
| 5,348,020 | A | 9/1994 | Hutson |
| RE35,122 | E | 12/1995 | Corenman et al. |
| 5,474,078 | A | 12/1995 | Hutson |
| 5,662,105 | A | 9/1997 | Tien |
| 5,795,304 | A | 8/1998 | Sun et al. |
| 5,827,195 | A | 10/1998 | Lander |
| 5,924,980 | A | 7/1999 | Coetzee |
| 5,971,930 | A | 10/1999 | Elghazzawi et al. |
| 6,002,952 | A | 12/1999 | Diab et al. |
| 6,067,462 | A | 5/2000 | Diab et al. |
| 6,094,592 | A | 7/2000 | Yorkey et al. |
| 6,122,535 | A | 9/2000 | Kastle et al. |
| 6,135,952 | A | 10/2000 | Coetzee |
| 6,347,245 | B1 * | 2/2002 | Lee et al. .................. 600/523 |
| 6,430,525 | B1 | 8/2002 | Weber et al. |
| 6,631,281 | B1 | 10/2003 | Kastle |
| 6,650,918 | B2 | 11/2003 | Terr |
| 6,699,194 | B1 | 3/2004 | Diab et al. |
| 6,699,198 | B2 * | 3/2004 | Numajiri .................. 600/504 |
| 6,805,673 | B2 | 10/2004 | Dekker et al. |
| 6,896,661 | B2 | 5/2005 | Dekker et al. |
| 6,931,269 | B2 | 8/2005 | Terry |
| 7,001,337 | B2 | 2/2006 | Dekker et al. |
| 7,016,715 | B2 | 3/2006 | Stetson |
| 7,020,507 | B2 | 3/2006 | Scharf et al. |
| 7,079,888 | B2 | 7/2006 | Oung et al. |
| 7,139,599 | B2 | 11/2006 | Terry |
| 7,212,847 | B2 | 5/2007 | Petersen et al. |
| 7,507,207 | B2 * | 3/2009 | Sakai et al. .................. 600/485 |
| 7,519,488 | B2 | 4/2009 | Fu et al. |
| 7,599,733 | B1 * | 10/2009 | Wirasinghe et al. .......... 600/510 |
| 7,620,448 | B1 * | 11/2009 | Farazi et al. .................. 600/515 |
| 7,949,390 | B1 * | 5/2011 | Wirasinghe et al. .......... 600/515 |
| 8,235,911 | B2 * | 8/2012 | Watson et al. ............... 600/502 |
| 8,239,780 | B2 * | 8/2012 | Manetta et al. ............... 715/764 |
| 2003/0225337 | A1 | 12/2003 | Scharf et al. |
| 2004/0039273 | A1 | 2/2004 | Terry |
| 2004/0073098 | A1 * | 4/2004 | Geva et al. .................. 600/300 |
| 2004/0127802 | A1 * | 7/2004 | Istvan et al. .................. 600/509 |
| 2004/0138538 | A1 | 7/2004 | Stetson |
| 2004/0171948 | A1 | 9/2004 | Terry |
| 2004/0181134 | A1 * | 9/2004 | Baker et al. .................. 600/336 |
| 2004/0204637 | A1 | 10/2004 | Fujii et al. |
| 2004/0210146 | A1 * | 10/2004 | Diab et al. .................. 600/502 |
| 2005/0049470 | A1 | 3/2005 | Terry |
| 2005/0085735 | A1 | 4/2005 | Baker, Jr. et al. |
| 2005/0240087 | A1 * | 10/2005 | Keenan et al. ............... 600/301 |
| 2006/0030766 | A1 | 2/2006 | Stetson |
| 2006/0094968 | A1 * | 5/2006 | Drew .......................... 600/509 |
| 2006/0122476 | A1 | 6/2006 | Van Slyke |
| 2006/0135860 | A1 * | 6/2006 | Baker et al. .................. 600/310 |
| 2006/0200016 | A1 | 9/2006 | Diab et al. |
| 2006/0211930 | A1 | 9/2006 | Scharf et al. |
| 2006/0225737 | A1 | 10/2006 | Iobbi |
| 2006/0241392 | A1 | 10/2006 | Feinstein et al. |
| 2007/0004977 | A1 * | 1/2007 | Norris .......................... 600/336 |
| 2007/0032732 | A1 * | 2/2007 | Shelley et al. ............... 600/504 |
| 2007/0282174 | A1 * | 12/2007 | Sabatino ...................... 600/300 |
| 2008/0036752 | A1 | 2/2008 | Diab et al. |
| 2008/0045809 | A1 * | 2/2008 | Hermannsson ............... 600/300 |
| 2008/0167564 | A1 | 7/2008 | Hete et al. |
| 2008/0208069 | A1 * | 8/2008 | John et al. .................... 600/509 |
| 2008/0243017 | A1 * | 10/2008 | Moussavi et al. ............ 600/532 |
| 2009/0030334 | A1 * | 1/2009 | Anderson et al. ............ 600/528 |
| 2009/0043216 | A1 * | 2/2009 | Lin et al. ...................... 600/501 |
| 2009/0192381 | A1 * | 7/2009 | Brockway et al. ........... 600/373 |
| 2009/0326351 | A1 * | 12/2009 | Addison et al. .............. 600/324 |
| 2010/0036271 | A1 * | 2/2010 | Wirasinghe et al. .......... 600/510 |
| 2010/0228102 | A1 * | 9/2010 | Addison et al. .............. 600/301 |
| 2010/0331715 | A1 * | 12/2010 | Addison et al. .............. 600/529 |

FOREIGN PATENT DOCUMENTS

| | | |
|---|---|---|
| WO | WO0176461 | 10/2001 |
| WO | WO2008096241 | 8/2008 |

OTHER PUBLICATIONS

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Poets, C. F., et al.; "Detection of movement artifact in recorded pulse oximeter saturation," *Eur. J. Pediatr.*; vol. 156, pp. 808-811 (1997).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Hayes, Matthew J., et al.; "Artifact reduction in photoplethysmography," *Applied Optics*, vol. 37, No. 31, pp. 7437-7446 (Nov. 1998).

Todd, Bryan, et al.; "The Identification of Peaks in Physiological Signals," *Computers and Biomedical Research*, vol. 32, pp. 322-335 (1999).

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1999).

Kaestle, S.; "An Algorithm for Reliable Processing of Pulse Oximetry Signals Under strong Noise Conditions," *Dissertation Book*, Lubeck University, Germany (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Kaestle, S.; "Determining Artefact Sensitivity of New Pulse Oximeters in Laboratory Using Signals Obtained from Patient," *Biomedizinische Technik*, vol. 45 (2000).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2000).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

(56) References Cited

OTHER PUBLICATIONS

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Yoon, Gilwon, et al.; Multiple diagnosis based on Photoplethysmography: hematocrit, SpO2, pulse and respiration, *Optics in Health Care and Biomedical optics: Diagnostics and Treatment; Proceedings of the SPIE*, vol. 4916; pp. 185-188 (2002).

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Johansson, A.; "Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 2004, pp. 2153-2156.

Matsuzawa, Y., et al.; "Pulse Oximeter," *Home Care Medicine*, pp. 42-45 (Jul. 2004); (Article in Japanese—contains English summary of article).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Huang, J., et al.; "Low Power Motion Tolerant Pulse Oximetry," *Abstracts*, A7, p. S103. (undated).

Lang, P., et al.; "Signal Identification and Quality Indicator™ for Motion Resistant Pulse Oximetry," *Abstracts*, A10, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al., "Signal Processing Using Fourier & Wavelet Transform," pp. II-310-II-311 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

Neumann, R., et al.; "Fourier Artifact suppression Technology Provides Reliable $SpO_2$," *Abstracts*, A11, p. S105. (undated).

\* cited by examiner

SIGNAL PROCESSING WARPING TECHNIQUE

RELATED APPLICATION

This application claims the benefit of U.S. Provisional Application No. 61/245,571, filed Sep. 24, 2009, which application is hereby incorporated by reference.

BACKGROUND

The present disclosure relates generally to medical devices and, more particularly, to methods of analyzing physiological parameters using signal processing warping techniques.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption of the transmitted light in such tissue. A typical pulse oximeter may use light emitting diodes (LEDs) to measure light absorption by the blood. The absorbed and/or scattered light may be detected by the pulse oximeter, and may result in a signal that is proportional to the intensity of the detected light. The received signal may be further processed, and various physiological parameters may be determined based on signal features.

The accuracy of physiological parameters determined based on the received signal may depend on a number of factors. For example, light absorption characteristics may vary depending on factors such as the location of the sensor and/or the physiology of the patient being monitored. Additionally, various types of noise and interference that can also affect accuracy may include electrical noise, physiological noise, patient motion, or other interferences. Some sources of noise are consistent, predictable, and/or minimal, while other sources of noise may be erratic, and may cause major interruptions in measuring blood flow characteristics. For example, motion of the patient may be unpredictable, and may cause interruptions that do not correspond to changes in the physiological parameters being measured. Methods of signal processing and/or signal analysis which enables the identification of non-physiological signal characteristics, such as motion, may improve the accuracy of pulse oximetry analyses.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
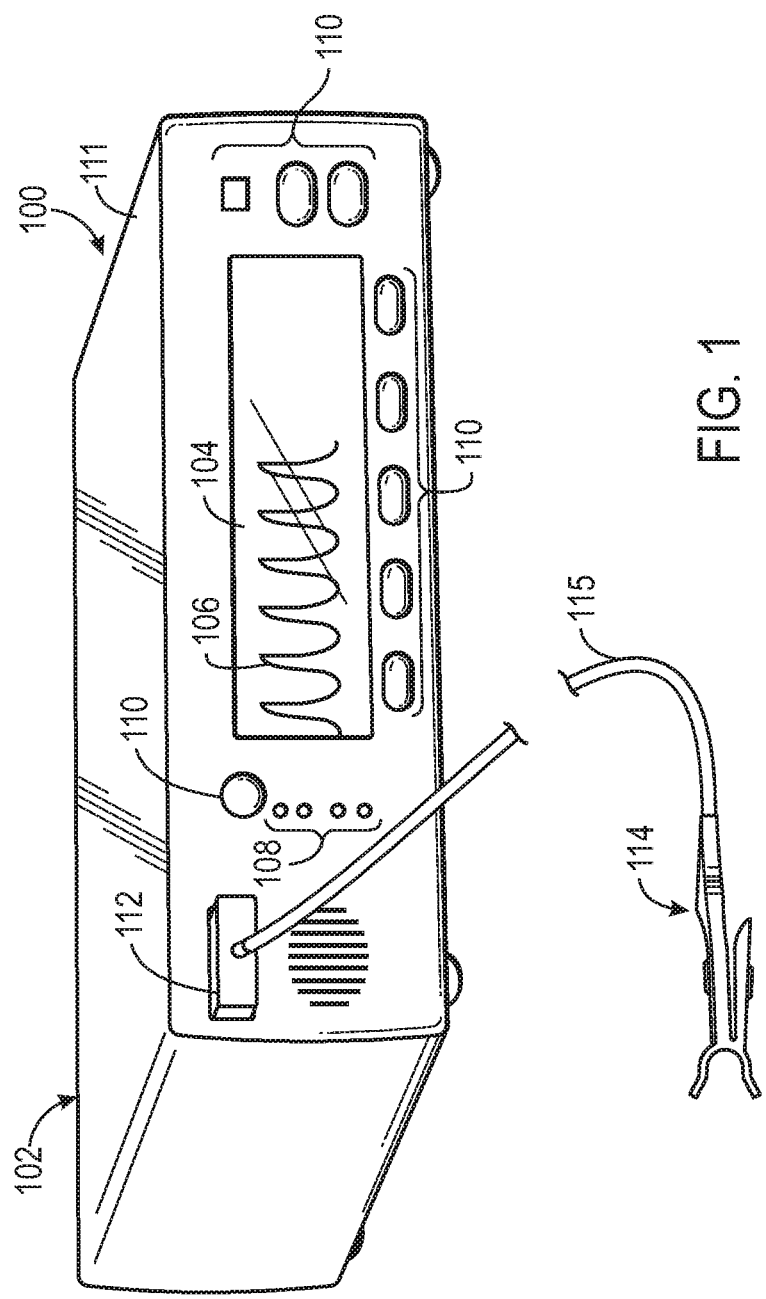
FIG. 1 illustrates a perspective view of a pulse oximeter in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to estimating physiological parameters related to blood flow and/or oxygenation in a patient by warping a physiological signal, such as a plethysmographic (pleth) signal. In one embodiment, the physiological signal may be analyzed in the time and frequency domain and non-physiological interferences may be identified using the warped physiological signal. More specifically, the physiological signal may be warped based on the energy density of the signal. Signal quality indicators, or signals used to determine the signal quality metrics (i.e., a quantification of the quality or accuracy) of the physiological signal, may likewise be warped using the same function to maintain scale invariance between the physiological signal and the signal quality indicator. By comparing the warped physiological signal with the warped signal quality indicator, non-physiological noise may be identified and/or removed.

In one or more embodiments, a physiological monitoring system, such as a pulse oximeter, may be used to estimate physiological parameters based on signals received from a sensor which correspond to a measured or observed characteristic of a patient. Estimating physiological parameters may be affected by the reliability of the received signals. For example, a reliable signal may result in a more accurate estimate. The reliability of the received signal may be affected by light absorption characteristics (i.e., the absorption of the emitted light by the patient's tissue), which may typically vary from patient to patient depending on their physiology and/or condition. The absorption characteristics may also vary depending on the location (e.g., the foot, finger, ear, etc.) where the sensor is applied, and whether there are possible interferences between the sensor and the tissue location (e.g., hair, nail polish, etc.). The design of the sensor or the application of the sensor may also affect the received signal. In one embodiment, the received signal may refer to a physiological signal corresponding to blood flow in a patient, such as a pleth signal. By way of illustration, such a pleth signal may be used herein as an example of a suitable physiological signal for processing in accordance with the present disclosure, though other physiological signals may also be suitable for such processing.

One method of determining whether a pleth signal or other physiological signal is reliable may be to qualify the signal by comparing it with various signal quality indicators. In one embodiment, the signal quality indicators may be derived using known patterns of a pleth signal, as well as known sources of signal noise. For example, in some embodiments, signal quality indicators may include signals indicative of an arterial pulse shape, consistency of a pulse shape, arterial pulse amplitude, modulation ratios of red to infrared modulations, and/or the period of an arterial pulse, etc. Such indicators may enable assessments of the presence of known error sources in the pleth signal. Furthermore, signal indicators may also include signal patterns of known noise sources. In some embodiments, signal indicators of known noise sources may enable the pulse oximeter to identify and remove noise sources, and/or provide feedback regarding which (if any) noise sources are affecting the measured signal. Signal patterns of known noise sources may include signals indicative of a low light level, optical interferences between the sensor and the tissue, light modulation other than the patient's tissue, improper positioning of the sensor on the tissue, and/or physical movement.

In some embodiments, the pleth signal may be processed to characterize the signal over a time-frequency plane. For example, certain processing operations such as Fourier transforms or wavelet transforms may be applied to represent the pleth signal in both the time domain and the frequency domain. Combining the time and frequency analyses may produce more information regarding a pleth signal's spectral components with regard to temporal locations. For example, applying Fourier transforms or wavelet transforms on a pleth signal may result in a spectrogram, which is a depiction of the spectral density of the signal. Applying certain transformations to the pleth signal may also enable the analysis of the signal amplitude, relative to both time and frequency. Further, time-frequency warp operators may be used, such that the original pleth signal and/or a time-frequency representation of the signal (e.g., a spectrogram) may be warped (e.g., stretched, compressed, or otherwise deformed) to further enable a pulse oximeter to identify certain signal characteristics. In one embodiment, signal quality indicators may also be warped according to the same warp operators applied to the pleth signal. By warping the time-frequency representations of the pleth signal and the signal quality indicators, certain non-physiological signal contributions or sources may be identified and/or removed, thereby improving the estimate of physiological parameters from the pleth signal.

Turning to FIG. 1, a perspective view of a medical device is illustrated in accordance with an embodiment. The medical device may be a pulse oximeter system 100. The pulse oximeter system 100 may include a monitor 102, such as those available from Nellcor Puritan Bennett LLC. The pulse oximeter system 100 may be utilized to observe the blood constituents of a patient's arterial blood to facilitate estimation of the state of oxygen exchange in the patient's body by emitting light into tissue and detecting the light after dispersion and/or reflection by the tissue. The amount of light that passes through the tissue and other characteristics of the light may vary in accordance with the changing amount of certain blood constituents in the tissue and the related light absorption and/or scattering. As with conventional pulse oximeter systems, the pulse oximeter system 100 may emit light from two or more LEDs or lasers into pulsatile tissue and then detect the transmitted light with a light detector (e.g., a photodiode or photo-detector) after the light has passed through the pulsatile tissue. Such measurements may be utilized to estimate a percentage of blood oxygen saturation in the probed volume of blood.

The monitor 102 may be configured to display calculated parameters on a display 104. As illustrated in FIG. 1, the display 104 may be integrated into the monitor 102. However, the monitor 102 may also be configured to provide data via a port to an external display or secondary monitor. The display 104 may be configured to display computed physiological data including, for example, an oxygen saturation percentage, a pulse rate, and/or a plethysmographic waveform 106. The oxygen saturation percentage may be a functional arterial hemoglobin oxygen saturation measurement in units of percentage $SpO_2$, while the pulse rate may indicate a patient's pulse rate in beats per minute. The monitor 102 may also display information related to alarms, monitor settings, and/or signal quality via indicator lights 108.

To facilitate user input, the monitor 102 may include a plurality of control inputs 110. The control inputs 110 may include fixed function keys, programmable function keys, and soft keys. Specifically, the control inputs 110 may correspond to soft key icons in the display 104. Pressing control inputs 110 associated with, or adjacent to, an icon in the display may select a corresponding option. The monitor 102 may also include a casing 111. The casing 111 may aid in the protection of the internal elements of the monitor 102 from damage.

The monitor 102 may further include a sensor port 112. The sensor port 112 may allow for connection to an external sensor 114, via a cable 115 which connects to the sensor port 112. The sensor 114 may be of a disposable or a non-disposable type. Furthermore, the sensor 114 may obtain readings from a patient, which can be used by the monitor to calculate certain physiological characteristics such as the blood-oxygen saturation of hemoglobin in arterial blood, the volume of individual blood pulsations supplying the tissue, and/or the rate of blood pulsations corresponding to each heartbeat of a patient.

Figure 2:
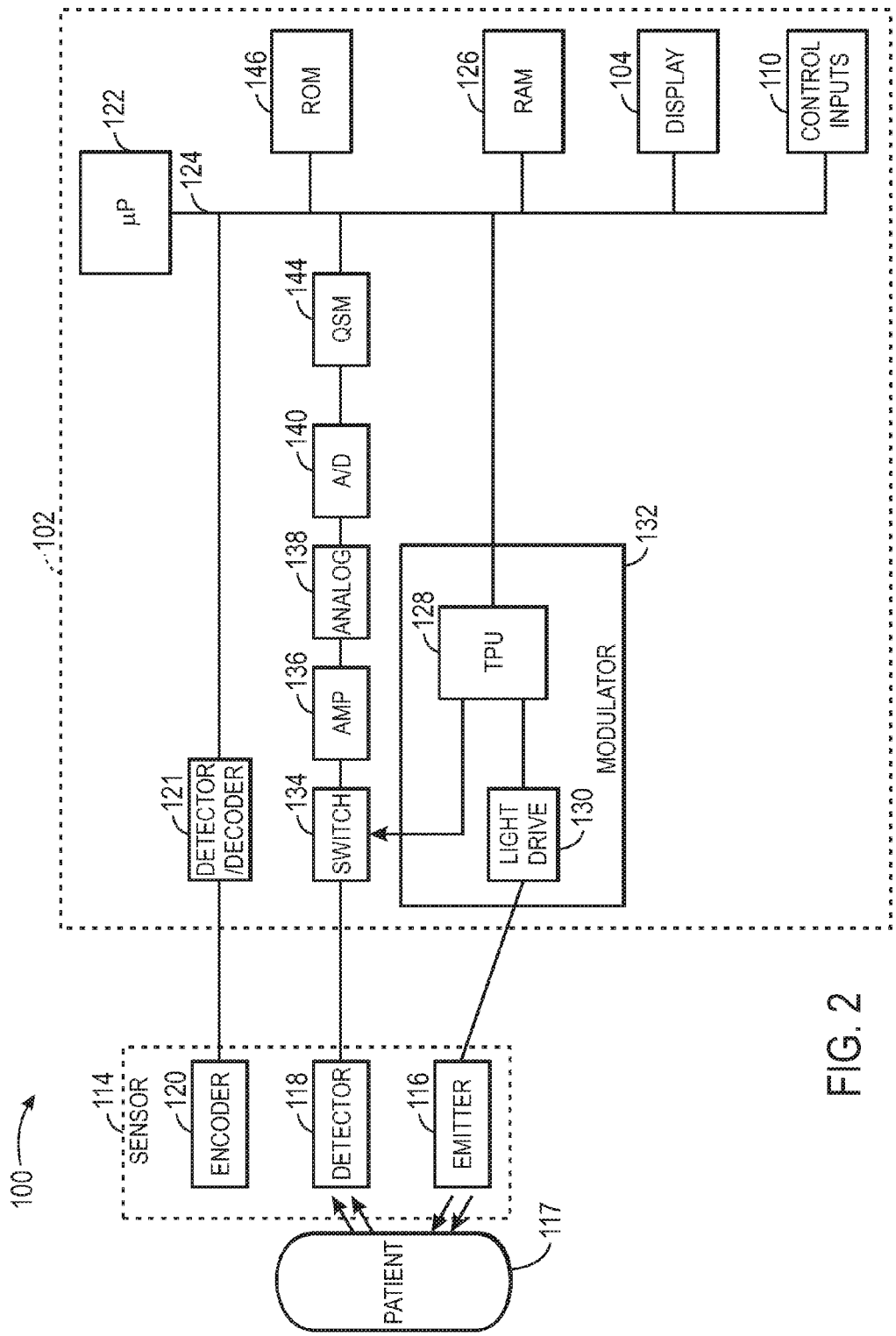
FIG. 2 illustrates a simplified block diagram of a pulse oximeter, according to an embodiment.

Turning to FIG. 2, a simplified block diagram of a pulse oximeter system 100 is illustrated in accordance with an embodiment. Specifically, certain components of the sensor 114 and the monitor 102 are illustrated in FIG. 2. The sensor 114 may include an emitter 116, a detector 118, and an encoder 120. The emitter 116 may receive modulated drive signals from the monitor 102, and may activate and deactivate a light emitting device at certain intervals. For example, the monitor 102 may activate and deactivate components that emit light of different wavelengths, such that light of different wavelength is alternately emitted.

The emitter 116 may be capable of emitting one or more wavelengths of light, e.g., RED and infrared (IR) light, into the tissue of a patient 117, where the RED wavelength may be between about 600 nm and about 700 nm, and the IR wavelength may be between about 800 nm and about 1000 nm. The emitter 116 may include a single emitting device, for example, with two light emitting diodes (LEDs) or the emitter 116 may include a plurality of emitting devices with, for example, multiple LED's at various locations. Regardless of the number of light emitting devices, the emitter 116 may be used to measure, for example, blood oxygen saturation, water fractions, hematocrit, or other physiologic parameters of the patient 117, as discussed herein. It should be understood that, as used herein, the term "light" may refer to one or more of radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use in accordance with the present disclosure.

In one embodiment, the detector 118 may be an array of detector elements that may be capable of detecting light at various intensities and wavelengths. In operation, light enters the detector 118 after passing through the tissue of the patient 117. The detector 118 may convert the light at a given intensity, which may be directly related to the absorbance and/or reflectance of light in the tissue of the patient 117, into an electrical signal. That is, when more light at a certain wavelength is absorbed or reflected, less light of that wavelength is typically received from the tissue by the detector 118. For example, the detector 118 may include one or more photodiodes, or any other element capable of converting light into either a current or voltage. After converting the received light to an electrical signal, the detector 118 may send the signal, which may be a pleth signal, to the monitor 102, where physiological characteristics may be calculated based at least in part on the absorption of light in the tissue of the patient 117.

In some embodiments, the sensor 114 may include an encoder 120, which may contain information about the sensor 114, such as what type of sensor it is (e.g., whether the sensor is intended for placement on a forehead or digit) and the wavelengths of light emitted by the emitter 116. This information may allow the monitor 102 to select appropriate algorithms and/or calibration coefficients for calculating the patient's 117 physiological characteristics. The encoder 120 may, for instance, be a memory on which one or more of the following information may be stored for communication to the monitor 102: the type of the sensor 114; the wavelengths of light emitted by the emitter 116; and the proper calibration coefficients and/or algorithms to be used for calculating the patient's 117 physiological characteristics. In one embodiment, the data or signal from the encoder 120 may be decoded by a detector/decoder 121 in the monitor 102.

Signals from the detector 118 and the encoder 120 may be transmitted to the monitor 102. The monitor 102 may include one or more processors 122 coupled to an internal bus 124. Also connected to the bus 124 may be a RAM memory 126, a ROM memory 146, and a display 104. The monitor 102 may also include a modulator 132, which may include a time processing unit (TPU) 128 and light drive circuitry 130. The modulator 132 may modulate the drive signals that activate the LEDs or other emitting structures of the emitter 116. The modulator 132 may be hardware-based, software-based, or some combination thereof. For example, a software aspect of the modulator 132 may be stored on the memory 126 and may be controlled by the processor 122. The TPU 128 may include a sine wave generator, and may provide timing control signals to light drive circuitry 130, which controls when the emitter 116 is activated, and if multiple light sources are used, the multiplexed timing for the different light sources. TPU 128 may also control the gating-in of signals from detector 118 through a switching circuit 134. These signals are sampled at the proper time, depending at least in part upon which of multiple light sources is activated, if multiple light sources are used.

The received signal from the detector 118 may be processed to provide certain physiological data. In one embodiment, the received signal may be passed through an amplifier 136, a low pass filter 138, and an analog-to-digital converter (ADC) 140 for amplifying, filtering, and digitizing the electrical signals the from the sensor 114. The digital data may then be stored in a queued serial module (QSM) 142, for later downloading to RAM 126 as QSM 142 fills up. There may also be multiple parallel paths for separate amplifiers, filters, and A/D converters for multiple light wavelengths or spectra received. Further, the processor 122 may calculate the oxygen saturation based on the received signals corresponding to the light received by the detector 118. For example, the processor 122 may perform instructions or algorithms stored on the memory 144, and may be configured to perform calculations to estimate physiological parameters based on the received signals.

In accordance with the present embodiments, the processor 122 may perform signal quality analyses using signal quality indicators stored on the memory 144 or in another location accessible by the processor 122. Furthermore, the processor 122 may perform other processing operations (e.g., Fourier transforms or wavelet transforms, etc.), and may use time-frequency warping to analyze a received signal. For example, the processor 122 may apply warp operators to identify and/or remove non-physiological noise from the received signal to produce a more accurate signal. In some embodiments, the more accurate signal may undergo further processing and/or calculations to produce physiological data.

As discussed, the received signals at the detector 118, such as a pleth signal, may include information for calculating certain physiological parameters and may also include signal components resulting from non-physiological conditions. For example, the physiology of the patient's tissue, the type of sensor, and movement of the patient may all result in a pleth signal that is less reliable, or less likely to produce accurate estimates of physiological parameters. In one or more embodiments, the pleth signal may be analyzed in the time and frequency domain, and warped according to the energy density of the signal. The same warping function may be applied to signal quality indicators, such that scale invariance may be maintained between the pleth signal and the signal quality indicators. Based on a comparison between the warped pleth signal and warped signal quality indicators, non-physiological wave components may be identified. In some embodiments, these wave components may be removed, or further used by the pulse oximeter system 100 to provide feedback to a user (e.g., a patient 117 or any person monitoring the patient 117) as to likely noise sources which may be interfering with obtaining accurate physiological data.

Figure 3:
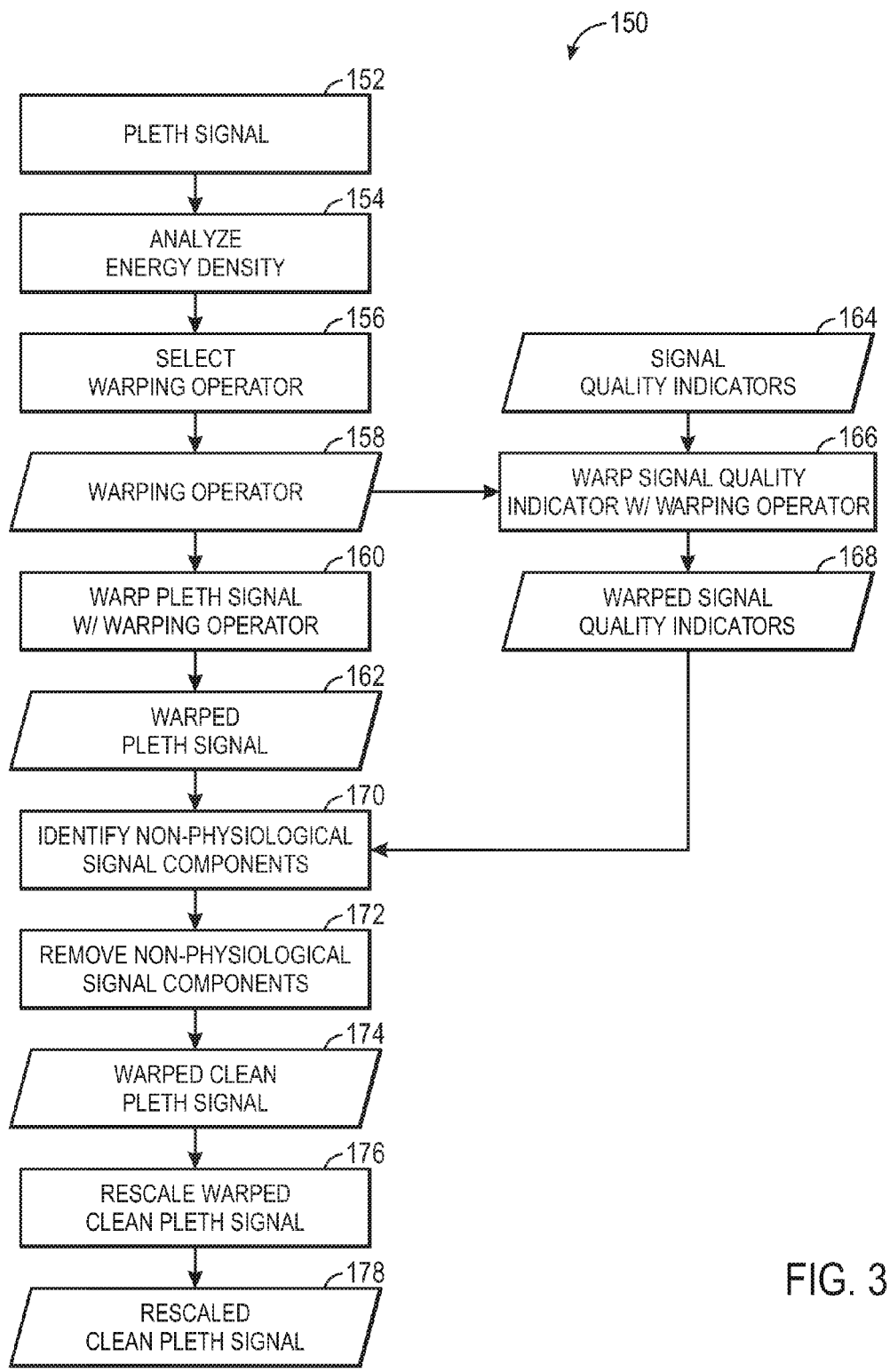
FIG. 3 is a flow chart depicting a process for identifying non-physiological noise in a plethysmographic (pleth) signal, according to an embodiment.

One example of an algorithm or process 150 using time and frequency warping to analyze a pleth signal is depicted in the flow chart of FIG. 3. In one embodiment, a pleth signal 152 may be output from a detector 118 (from FIG. 2). The pleth signal 152 may be a signal proportional to the intensity of light emitted from the emitter 116, transmitted and/or scattered through the tissue, and received at the detector 118. The pleth signal 152 may be an example of any type of signal received at the detector 118 which may be decoded, processed, and/or calculated to determine various physiological parameters of the patient 117 (e.g., oxygen saturation, pulse rate, etc.). The pleth signal 152 may also include non-physiological signal components resulting from noise sources such as patient physiology, sensor type, incorrect sensor placement, and/or movement of the patient 117. The non-physiological signal components in the pleth signal 152 may decrease the reliability of the signal 152 as noise may decrease the likelihood of accurately estimating certain physiological data.

In one embodiment, a monitor 102 may analyze the energy density of the pleth signal 152 (block 154). Analyzing the energy density of the pleth signal 152 may include analyzing the changes in energy density of the signal 152. To analyze changes in energy density, the signal 152 may be transformed to be represented in the time and/or frequency domains. In one embodiment, a time and frequency representation of the pleth signal 152 may enable the analysis of signal amplitude with respect to both time and frequency. For example, representations of a time and frequency signal, such as a spectrogram, may provide the spectral density of the signal with respect to time (typically x-axis) and frequency (typically y-axis).

A pleth signal 152 may vary from patient to patient, or vary depending on the type or location of the sensor. Thus, the energy density of the signal 152 may vary, and may have different signal characteristics (e.g., amplitude, frequency, noise, etc.) The monitor 102 may analyze the energy density (block 154) of the signal 152 to determine how the signal 152 may be warped to facilitate analysis. The monitor 102 may select a warping operator 158 (block 156) to warp the signal 152 (block 160). For example, the warping function 158 may stretch the signal 152 to make certain features more discernable. By analyzing the features of the warped pleth signal 162, certain non-physiological signal components may be identified.

The process 150 may also involve analyzing the warped pleth signal 162 in conjunction with signal quality indicator(s) 164. As previously discussed, signal quality indicators 164 may be signals derived based on known patterns of a pleth signal 152, as well as known patterns of signal noise. Such signal quality indicators 164 may enable assessments of the presence of known error sources in the pleth signal 152 by analyzing the wave patterns of the warped pleth signal 162 in view of the signal quality indicators 164. To maintain scale invariance between the warped pleth signal 162 and the signal quality indicators 164, the signal quality indicators 164 may also be warped based on the same operator 158 selected to warp the pleth signal 152 (block 166).

By warping the signal quality indicators 164 by the same operator 158, the warped signal quality indicators 168 and the warped pleth signal 162 may have the same time scale, such that frequency and/or amplitude characteristics of the warped pleth signal 162 and the warped signal quality indicators 168 may be compared with the same temporal frame of reference. As the signal quality indicators 164 may have signal characteristics based on known patterns of signal noise (e.g., physical movement of a patient), the monitor 102 may analyze the warped pleth signal 162 based on the warped signal quality indicator 168 to identify such signal noise components in the warped pleth signal 162 (block 170). Furthermore, the time-frequency warping may improve pleth signal analyses, as some non-physiological signal components may be accounted for with respect to time and frequency. For example, signal irregularities such as physical movement of a patient may have signal characteristics which may be identified based on their temporal components. While some transformations of the pleth signal 152 may result in globally averaged energy value without information regarding the temporal components of the signal 152, in one implementation a transformation (such as a wavelet transformation) may be employed that allows both time and frequency components to be analyzed. Such an approach may facilitate the identification of some non-physiological signal components.

The warped signal quality indicator 168 and the warped pleth signal 162 may be analyzed using a suitable process for comparing and/or distinguishing signal characteristics, which may indicate certain physiological or non-physiological signal components in the warped pleth signal 162. For example, in one or more embodiments, analyzing the signals may include cross-correlating the warped signal quality indicator 168 with the warped pleth signal 162, and determining whether any portion of the cross-correlated signal surpasses a threshold (e.g., an intensity threshold on a cross-correlated spectrogram), indicating an occurrence of a known physiological or non-physiological signal component.

In one embodiment, if the monitor 102 identifies a non-physiological signal component (block 170) in the warped pleth signal 162, the monitor 102 may remove the non-physiological signal component (block 172). The warped and "clean" pleth signal 174 may then be rescaled (block 176), such that the rescaled clean pleth signal 178 may be used for further processing, and physiological parameters may be calculated using the rescaled clean pleth signal 178 having the non-physiological signal components removed. Identifying and/or removing non-physiological signal components may result in a more reliable rescaled pleth signal 178, increasing the likelihood of making more accurate estimates of physiological parameters.

In another embodiment, the monitor 102 may indicate that noise is affecting the measurement upon the identification of non-physiological signal components at block 170. Further, in some embodiments, the monitor 102 may provide more specific feedback regarding the quality of the signal, including indicating a cause of the noise affecting the measurement. For example, the monitor 102 may use multiple signal quality indicators 164, and may analyze a pleth signal 152 with more than one signal quality indicator 164, each identifying one or more physiological or non-physiological conditions. If the monitor 102 determines that non-physiological signal components are present in the warped pleth signal 162 based on an analysis with a signal quality indicator, the monitor 102 may provide feedback as to the source of the non-physiological signal component. For example, if a warped signal quality indicator 164 associated with patient motion corresponds to signal components of the warped pleth signal 162, the monitor 102 may indicate that motion is affecting the accuracy of the pulse oximetry measurement.

Although the above process 150 discusses time-frequency warping and use of signal quality indicators to identify non-physiological signal components, another process in accordance with the present techniques may utilize algorithms, for example, neural network software algorithms, such that some processing steps may be eliminated or streamlined. For example, in some embodiments, the monitor 102 may use a learning algorithm to train a neural network to recognize certain signal characteristics as non-physiological signal components. A neural network of recognized non-physiological signal components may save processing time, as certain signals may not need to be warped in order to identify the occurrence or type of non-physiological noises in the pleth signal 152. For example, a monitor 102 may initially warp a pleth signal 152 and use a warped signal quality indicator 168 to identify and/or remove a non-physiological signal component, as outlined in the process 150 above. Once the monitor 102 identifies the non-physiological signal component, future occurrences of the non-physiological signal component may be identified without applying all the steps of the process 150. In one embodiment, the monitor 102 may identify a previously identified non-physiological component in a warped pleth signal 162 without using signal quality indicators. Furthermore, in one embodiment, the monitor 102 may identify a non-physiological component in an unwarped pleth signal 152 without warping and/or without using signal quality indicators.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A method for measuring a physiological parameter of a human, comprising the acts of:
   analyzing, by using a processor, an energy density of a signal having a physiological component and a non-physiological component to determine one or more changes in the energy density of the signal over time;
   determining, by using the processor, based on the one or more changes in the energy density of the signal over time, a warping function configured to enable identification of characteristics of the signal corresponding to the non-physiological component;
   stretching or compressing along a time scale, by using the processor, the signal having the physiological component and the non-physiological component by using the warping function to produce a warped signal;
   stretching or compressing, by using the processor, a signal quality indicator by using the warping function to produce a warped signal quality indicator;
   identifying, by using the processor, the non-physiological component of the signal based on an analysis of the warped signal with the warped signal quality indicator; and
   using the physiological component of the signal and disregarding the non-physiological component of the signal to determine the physiological parameter.

2. The method, as set forth in claim 1, comprising warping a signal quality indicator with the warping function, and wherein identifying the non-physiological signal component is based on an analysis of the warped signal and a warped signal quality indicator.

3. The method, as set forth in claim 2, wherein the signal quality indicator comprises one or more signals derived from known physiological and non-physiological signal characteristics.

4. The method, as set forth in claim 2, wherein the signal quality indicator comprises one or more signals indicative of optical interference, undesired light modulation, physical movement of a patient, or improper sensor placement.

5. The method, as set forth in claim 1, wherein the signal comprises a plethysmographic signal or a spectrogram corresponding to the plethysmographic signal.

6. The method, as set forth in claim 1, comprising indicating the presence of the non-physiological component on a pulse oximeter measuring the signal.

7. The method, as set forth in claim 1, comprising indicating a source of the non-physiological component on a pulse oximeter measuring the signal.

8. The method, as set forth in claim 1, comprising using the non-physiological component in a neural network and identifying future occurrences of the non-physiological component based on the neural network.

9. A method for measuring a physiological parameter of a human, comprising the acts of:
   analyzing, by using a processor, an energy density of a signal having a physiological component and a non-physiological component to determine one or more changes in the energy density of the signal over time;
   determining, by using the processor, based on the one or more changes in the energy density of the signal over time, a warping function configured to enable identification of characteristics of the signal corresponding to the non-physiological component;
   stretching or compressing along a time scale, by using the processor, the signal having the physiological component and the non-physiological component by using the warping function to produce a warped signal;
   stretching or compressing along a time scale, by using the processor, a signal quality indicator by using the warping function to produce a warped signal quality indicator;
   analyzing, by using the processor, the warped signal and the warped signal quality indicator;
   identifying, by using the processor, the non-physiological component of the signal based on the analysis of the warped signal and the warped signal quality indicator; and
   using the physiological component of the signal and disregarding the non-physiological component of the signal to determine the physiological parameter.

10. The method, as set forth in claim 9, wherein analyzing the warped signal and the warped signal quality indicator comprises analyzing the two signals in a common time scale.

11. The method, as set forth in claim 10, wherein analyzing the warped signal and the warped signal quality indicator comprises cross-correlating the two signals.

12. The method, as set forth in claim 11, wherein identifying the non-physiological component comprises determining whether a cross-correlation of the two signals indicates a non-physiological component.

13. The method, as set forth in claim 12, wherein the non-physiological component is identifiable based on whether a portion of the cross-correlation surpasses a threshold.

14. The method, as set forth in claim 9, wherein identifying the non-physiological signal component comprises comparing a scalogram of the warped signal with a scalogram of the warped signal quality indicator.

15. A pulse oximetry system, comprising:
   data processing circuitry configured to:
      analyze a three dimensional time-frequency representation of a signal comprising a physiological component and a non-physiological component to determine one or more changes in the energy density of the signal over time, to determine, based on the one or more changes in the energy density of the signal over time, a warping operator configured to enable identification of the non-physiological component;
      warp the signal, via the processor, with the warping operator to produce a warped signal;

warp a signal quality indicator, via the processor, with the warping operator to produce a warped signal quality indicator;

identify the non-physiological component of the signal based on a comparison of the warped signal and the warped signal quality indicator; and determine a physiological parameter by disregarding the non-physiological component of the signal and by using the physiological component of the signal.

16. The pulse oximetry system of claim 15, wherein the signal comprises a plethysmographic signal or a spectrogram corresponding to the plethysmographic signal.

17. The pulse oximetry system of claim 15, wherein the data processing circuitry is further configured to warp a signal quality indicator with the warping operator to produce a warped signal quality indicator.

18. The pulse oximetry system of claim 17, wherein the data processing circuitry is configured to compare the warped signal and the warped signal quality indicator to identify the non-physiological component of the signal.

19. The pulse oximetry system of claim 15, wherein the warping operator comprises an operator for stretching the signal along the time scale or a compressing operator for compressing the signal along the time scale.

20. The pulse oximetry system of claim 15, comprising a display on which the data processing circuitry displays an indication of the type or presence of the identified non-physiological component.

21. The method, as set forth in claim 1, wherein analyzing the energy density of the signal comprises characterizing the signal over a time-frequency plane to generate a three dimensional time-frequency representation of the signal, and analyzing the three dimensional time-frequency representation of the signal to determine the spectral density of the signal with respect to time and frequency.

* * * * *